(12) United States Patent
Schechter et al.

(10) Patent No.: US 10,154,877 B2
(45) Date of Patent: Dec. 18, 2018

(54) ENDOSCOPIC SURGICAL INSTRUMENT (71) Applicant: COVIDIEN LP, Mansfield, MA (US)

(72) Inventors: David A. Schechter, Boulder, CO (US);
Nathan White, Longmont, CO (US);
Joshua K. Goetz, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 476 days.

(21) Appl. No.: 14/932,302

(22) Filed: Nov. 4, 2015

(65) Prior Publication Data
US 2017/0119459 A1 May 4, 2017

(51) Int. Cl.
*A61B 18/14* (2006.01)
*A61B 34/37* (2016.01)
(Continued)

(52) U.S. Cl.
CPC .......... *A61B 18/1445* (2013.01); *A61B 34/37* (2016.02); *A61B 2017/294* (2013.01); *A61B 2017/2936* (2013.01); *A61B 2017/2947* (2013.01); *A61B 2018/0063* (2013.01); *A61B 2018/00428* (2013.01); *A61B 2018/1455* (2013.01)

(58) Field of Classification Search
CPC ........ A61B 18/1445; A61B 2017/2936; A61B 2017/294; A61B 2017/2947; A61B 2017/2932; A61B 2017/2937; A61B 2017/2926; A61B 2017/2919; A61B 2017/2931; A61B 2017/2939; A61B 2017/2913
See application file for complete search history.

(56) References Cited

U.S. PATENT DOCUMENTS

D249,549 S  9/1978  Pike
D263,020 S  2/1982  Rau, III
(Continued)

FOREIGN PATENT DOCUMENTS

CN  201299462     9/2009
DE  2415263 A1  10/1975
(Continued)

OTHER PUBLICATIONS

U.S. Appl. No. 14/098,953, filed Dec. 6, 2013; inventor: Cunningham.
(Continued)

*Primary Examiner* — Michael Peffley (57) ABSTRACT

An endoscopic surgical instrument is provided. The instrument includes a housing, a handle, an elongated shaft extending distally from the housing and defining a longitudinal axis, an end effector assembly, a drive assembly, a clevis, a first link, and a second link. The end effector assembly is disposed adjacent a distal end of the elongated shaft and includes a first jaw member and a second jaw member. The first link is pivotably connected to the clevis about a first pivot axis, and is pivotably connected to the first jaw member about a first jaw member pivot. The second link is pivotably connected to the clevis about a second pivot axis, and is pivotably connected to the second jaw member about a second jaw member pivot. The first pivot axis and the second pivot axis are offset from the longitudinal axis.

22 Claims, 6 Drawing Sheets

(51) Int. Cl.
*A61B 18/00* (2006.01)
*A61B 17/29* (2006.01)

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manna | |
| D299,413 S | 1/1989 | DeCarolis | |
| 5,133,736 A * | 7/1992 | Bales, Jr. | A61B 10/06 600/564 |
| 5,170,800 A | 12/1992 | Smith et al. | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,695,521 A | 12/1997 | Anderhub | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| 6,168,605 B1 | 1/2001 | Measamer et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,083,618 B2 * | 8/2006 | Couture | A61B 18/1445 606/49 |
| 7,101,371 B2 * | 9/2006 | Dycus | A61B 18/1445 606/205 |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |

| | | | |
|---|---|---|---|
| 8,469,993 B2 * | 6/2013 | Rothberg | A61B 10/06 600/564 |
| 2008/0015566 A1 | 1/2008 | Livneh | |
| 2014/0188101 A1 | 7/2014 | Bales, Jr. et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 0712328 U1 | 2/1988 |
| DE | 3627221 A1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61501068 | 9/1984 |
| JP | 10-24051 A | 1/1989 |
| JP | 11-47150 A | 6/1989 |
| JP | 65502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |

(56) References Cited

FOREIGN PATENT DOCUMENTS

| | | |
|---|---|---|
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |
| WO | 2015017989 A1 | 2/2015 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Extended European Search Report for application No. 16 19 6996 dated Mar. 14, 2017.
Michael Choti, "Abdominoperineal Resection with the LigaSure Vessel Sealing System and LigaSure Atlas 20 cm Open Instrument" ; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps" , Feb. 6, 1967 (Feb. 6, 1965), British Medical Journal Feb. 5, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/ Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
U.S. Appl. No. 14/065,644, filed Oct. 29, 2013; inventor: Reschke.

\* cited by examiner

ENDOSCOPIC SURGICAL INSTRUMENT

BACKGROUND

Technical Field

The present disclosure relates to surgical instruments and, more particularly, to surgical instruments including jaw members for grasping, treating, sealing, stapling, and/or dividing tissue, and where the surgical instruments are configured for endoscopic use.

Description of Related Art

Many surgical instruments are known for sealing, stapling, or otherwise joining tissue. Some of these surgical include one or more movable handles, levers, actuators, triggers, etc. for actuating and/or manipulating one or more functional components of the surgical instrument. For example, a surgical forceps may include a movable handle that is selectively actuatable relative to a stationary handle for moving at least one jaw member with respect to another jaw member of the forceps between spaced-apart and approximated positions for grasping tissue therebetween. Such a forceps may further include additional triggers for selectively actuating electrosurgical energy or for deploying staples, and/or for deploying a knife between the jaw members to cut tissue grasped therebetween.

In certain types of surgical procedures, it may be useful to use an energy-based device during endoscopic, laparoscopic and other minimally invasive surgeries. Many challenges exist when attempting to make an energy-based surgical device below a certain diameter (e.g., 2.8 mm), such as the transmission of clamping pressure between the jaw members, the ability to transect the tissue between the jaw members, and the conduction of electrical current. Additionally, ensuring electrical isolation of tissue-contacting surfaces of jaw members is challenging for surgical instruments of the size (e.g., diameter) contemplated herein. Accordingly, a surgical instrument including these capabilities with a relatively small diameter may be useful.

SUMMARY

The present disclosure relates to an endoscopic surgical instrument, including a housing, a handle movably connected to the housing, an elongated shaft extending distally from the housing and defining a longitudinal axis, an end effector assembly, a drive assembly, a clevis, a first link, and a second link. The end effector assembly is disposed adjacent a distal end of the elongated shaft and includes a first jaw member and a second jaw member. At least one of the jaw members is movable with respect to the other jaw member from a spaced-apart position where the jaw members are spaced relative to one another to a grasping position where the jaw members are closer to one another for grasping tissue. The drive assembly is disposed at least partially within the housing and includes a drive bar extending at least partially through the elongated shaft such that longitudinal translation of the drive bar causes the jaw members to move between the spaced-apart position and the grasping position. The clevis is disposed adjacent a distal portion of the drive bar. The first link is pivotably connected to the clevis about a first pivot axis, and is pivotably connected to the first jaw member about a first jaw member pivot. The second link is pivotably connected to the clevis about a second pivot axis, and is pivotably connected to the second jaw member about a second jaw member pivot. The first pivot axis and the second pivot axis are offset from the longitudinal axis.

In aspects of the present disclosure, the first pivot axis and the second pivot axis are offset from the longitudinal axis by a distance of about 0.005 inches.

In other aspects, the first pivot axis is on a first side of the longitudinal axis, and the second pivot axis is on a second side of the longitudinal axis In yet other aspects, a diameter of the elongated shaft is about 2.4 mm. A majority of the elongated shaft may have a constant diameter of about 2.4 mm.

In still other aspects, the drive assembly is configured to apply pressure between the jaw members in the range of about 3 kg/cm$^2$ to about 16 kg/cm$^2$.

In aspects of the present disclosure, the first jaw member includes a support surface and an active electrode seal plate. The active electrode seal plate may be bonded to the support surface with a high-temperature, dielectric epoxy. The support surface may be coated with a high-temperature dielectric material.

In other aspects, at least a portion of the first jaw member is coated with a high-temperature dielectric material. In some aspects, an entirety of the second jaw member lacks a high-temperature dielectric material.

In yet other aspects, the first jaw member is connected to the second jaw member with a pivot pin. The pivot pin may be disposed distally of the first jaw member pivot In still other aspects, the first jaw member pivot is movable toward and away from the longitudinal axis.

In aspects of the present disclosure, the endoscopic surgical instrument further includes a knife configured to sever tissue. The first jaw member includes a knife slot defined therein and configured to guide longitudinal translation of the knife, and a proximal end of the knife slot is disposed proximally of the pivot pin. The first jaw member may include a tissue-contacting surface and a flange extending perpendicularly from the tissue-contacting surface, wherein the pivot pin extends through an opening in the flange. The flange includes a thickness of about 0.012 inches.

The present disclosure also relates to an endoscopic surgical instrument, including a housing, a handle movably connected to the housing, an elongated shaft extending distally from the housing and defining a longitudinal axis, an end effector assembly, and a drive assembly. The elongated shaft includes a diameter of about 2.4 mm along at least a majority of an entire length thereof. The end effector assembly is disposed adjacent a distal end of the elongated shaft and includes a first jaw member and a second jaw member. At least one of the jaw members is movable with respect to the other jaw member from a spaced-apart position wherein the jaw members are spaced relative to one another to a grasping position where the jaw members are closer to one another for grasping tissue. The drive assembly is disposed at least partially within the housing and includes a drive bar extending at least partially through the elongated shaft such that longitudinal translation of the drive bar causes the jaw members to move between the spaced-apart position and the closer position for grasping tissue. The drive assembly is configured to apply pressure between the jaw members in the range of about 3 kg/cm$^2$ to about 16 kg/cm$^2$.

In aspects of the present disclosure, at least a portion of the first jaw member is coated with a high-temperature dielectric material, and an entirety of the second jaw member lacks a high-temperature dielectric material.

BRIEF DESCRIPTION OF THE DRAWINGS

Various aspects of the present disclosure are described herein with reference to the drawings wherein like reference numerals identify similar or identical elements.

DETAILED DESCRIPTION

Embodiments of the presently disclosed surgical instrument are described in detail with reference to the drawings, in which like reference numerals designate identical or corresponding elements in each of the several views. As used herein the term "distal" refers to that portion of the surgical instrument that is farther from the user, while the term "proximal" refers to that portion of the surgical instrument that is closer to the user.

Figure 1:
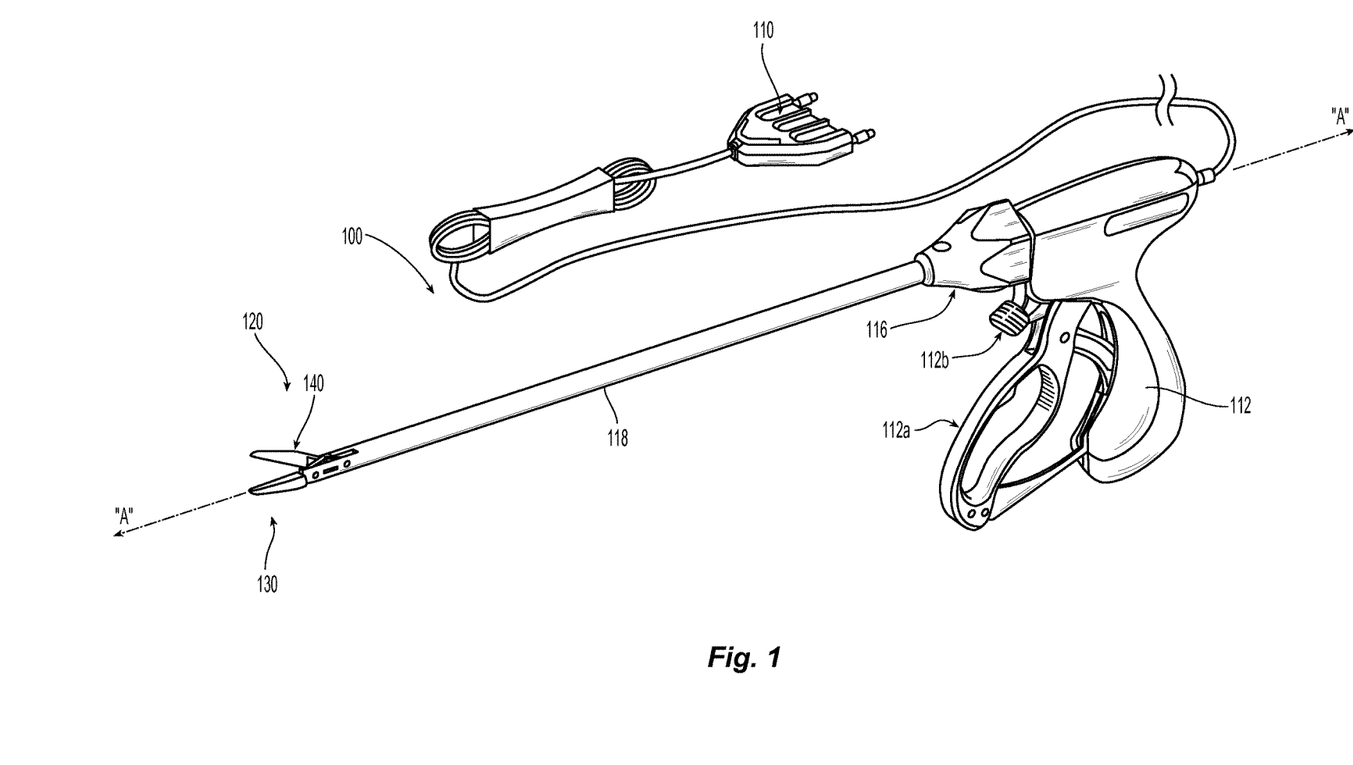
FIG. 1 is a perspective view of an embodiment of a surgical instrument in accordance with the present disclosure.

Referring initially to FIG. 1, an embodiment of a surgical instrument 100 is shown for use with various surgical procedures. Surgical instrument 100 may be configured to connect to a source of electrosurgical energy (not shown) via connector assembly 110, and/or may contain an independent energy source e.g., a battery (not shown). The use of an electrosurgical apparatus to apply electrosurgical energy to tissue is generally described in U.S. Pat. No. 7,083,618, which is incorporated herein in its entirety by reference.

Surgical instrument 100 includes a housing or handle assembly 112 near a proximal end, an end effector 120 near a distal end and an elongated shaft 118 extending therebetween. Elongated shaft 118 defines a longitudinal axis "A-A." The end effector 120 includes a first jaw member 130 and a second jaw member 140, which are movable relative to each other. The end effector 120 may be positioned within a body cavity to engage tissue at a surgical site while handle assembly 112 is manipulatable by a surgeon from outside the body cavity to control the movement and operation of the end effector 120. Handle assembly 112 includes a movable handle 112a, which is manipulatable to open and close the end effector 120, and a trigger 112b, which is manipulatable to initiate an electrosurgical current.

The present disclosure includes elongated shaft 118 having a relatively small diameter for use in minimally invasive surgical procedures. For example, the diameter of elongated shaft 118 may be about 2.4 mm.

Figure 2:
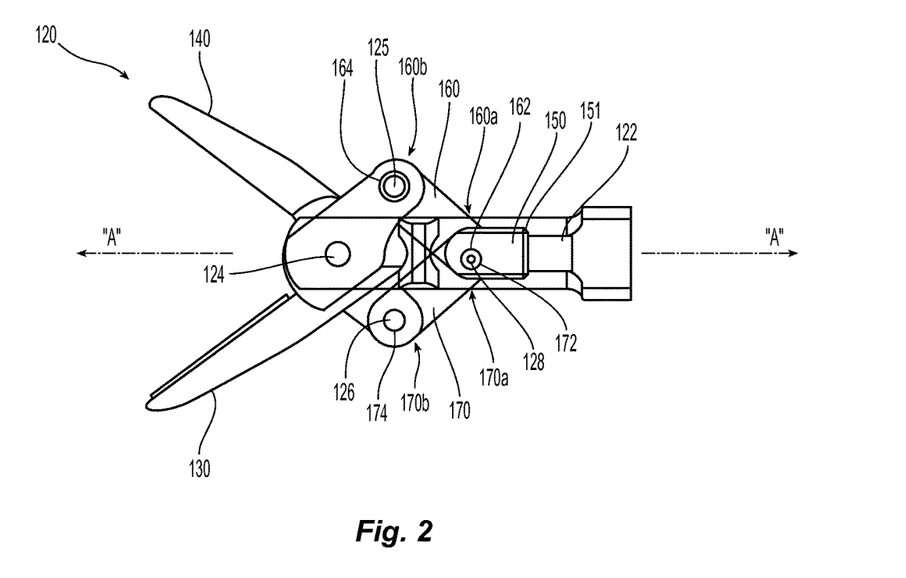
FIGS. 2 and 3 are side, cut-away views of an end effector of the surgical instrument of FIG. 1.

Actuation of the movable handle 112a longitudinally translates a drive bar or a control rod 122 (FIGS. 2 and 3) of a drive assembly (not shown) to apply a pressure between the jaw members 130 and 140 in the range of about 3 kg/cm$^2$ to about 16 kg/cm$^2$. Further, details of a vessel sealing device including a handle assembly and drive assembly for controlling actuation of an end effector can be found in U.S. Pat. Nos. 7,101,371 and 7,083,618, which are incorporated herein in their entirety by reference.

In the approximated configuration where tissue can be grasped between the jaw members 130, 140, a separation or gap distance is maintained between the jaw members 130, 140 by an array of stop members (not shown). In some embodiments, to provide an effective tissue seal, an appropriate gap distance of between about 0.001 inches to about 0.006 inches may be provided. The stop members may be positioned on at least one jaw member 130, 140 and may be made from a thermally sprayed ceramic (e.g. Alumina Titania), epoxy, or a high temperature plastic, for example. Other configurations are also contemplated.

To achieve the desired pressure applied between the jaw members 130 and 140 in surgical instrument 100 which includes a small-diameter elongated shaft 118 (e.g., about 2.4 mm), various design considerations are important. With particular reference to FIGS. 2-6, embodiments of end effector 120, and components thereof, in accordance with the present disclosure are shown.

With particular reference to FIGS. 2-6, the end effector 120 includes first jaw member 130, second jaw member 140, a clevis 150, a first link 160, and a second link 170. Generally, first link 160 is pivotally connected to clevis 150 and is pivotally connected to first jaw member 130, and second link 170 is pivotally connected to clevis 150 and is pivotally connected to second jaw member 140. Further, first jaw member 130 and second jaw member 140 are pivotally connected to each other.

Figure 5:
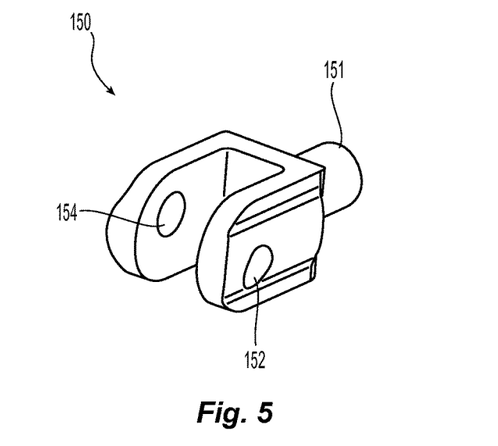
Figure 6:
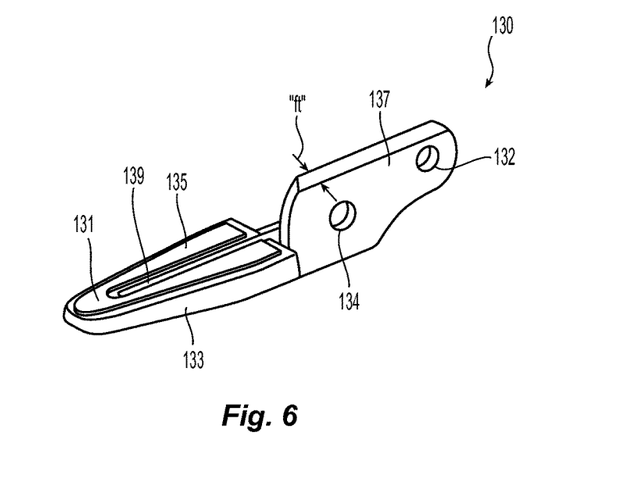
FIG. 6 is a perspective view of a jaw member of the surgical instrument of FIG. 1 in accordance with embodiments of the present disclosure.
Figure 8:
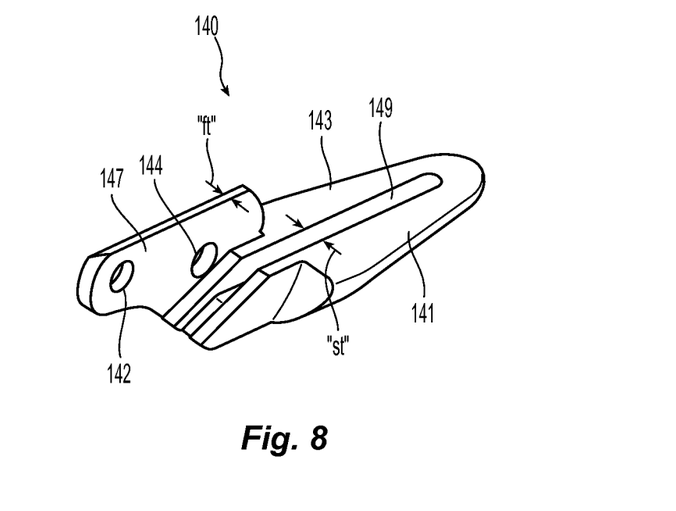
FIG. 8 is a perspective view of a jaw member of the surgical instrument of FIG. 1 in accordance with embodiments of the present disclosure.

More particularly, each jaw member 130, 140 respectively includes a proximal pivot opening 132, 142 and a distal pivot opening 134, 144 (see FIGS. 6 and 8, for example). Each link 160, 170 respectively includes a proximal pivot opening 162, 172 and a distal pivot opening 164, 174. Clevis 150 includes a first opening 152 and a second opening 154 (FIGS. 4 and 5).

Distal pivot opening 134 of first jaw member 130 is pinned to distal pivot opening 144 of second jaw member 140 by a pivot pin 124. Proximal pivot opening 132 of first jaw member 130 is pinned to distal pivot opening 164 of first link 160 by a pivot pin 125. Proximal pivot opening 142 of second jaw member 140 is pinned to distal pivot opening 174 of second link 170 by a pivot pin 126. Proximal pivot opening 162 of first link 160 is pinned to first opening 152 of clevis 152 by a pivot pin 127 defining a first pivot axis. Proximal pivot opening 172 of second link 170 is pinned to second opening 154 of clevis 150 by a pivot pin 128 defining a second pivot axis. As such, first link 160 is pivotable with respect to clevis 150, and first link 160 is pivotable with respect to first jaw member 130; second link 170 is pivotable with respect to clevis 150, and second link 170 is pivotable with respect to second jaw member 140.

Control rod 122 is mechanically engaged with a proximal portion 151 of clevis 150, such that longitudinal translation of control rod 122 causes a corresponding longitudinal translation of clevis 150. More particularly, proximal translation of control rod 122 causes proximal translation of clevis 150, which causes proximal portions 160a, 170a of links 160, 170, respectively, to move proximally, which further causes respective distal portions 160b, 170b of links 160, 170 to move proximally and toward the longitudinal axis "A-A." This movement of links 160, 170 causes jaw members 130, 140 to pivot toward each other, e.g., to grasp tissue therebetween. Further, distal translation of control rod 122 causes distal translation of clevis 150, and results in jaw members 130, 140 being pivoted away from each other toward the open position.

Figure 3:
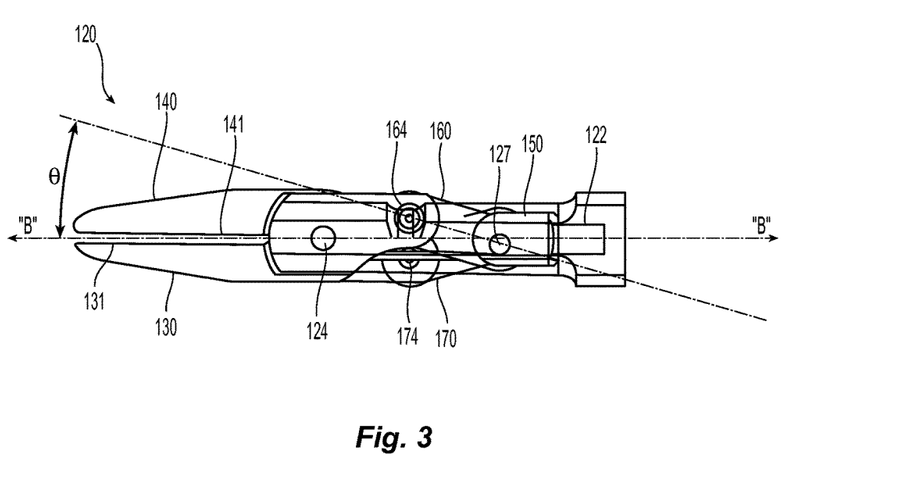
Figure 4:
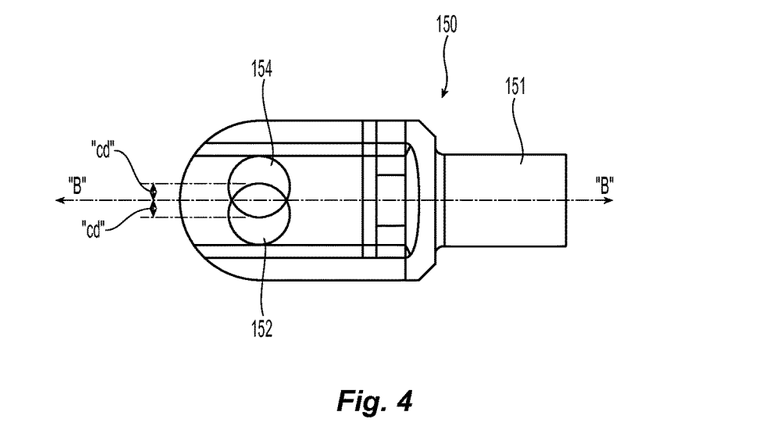
FIGS. 4 and 5 are various views of a clevis of the end effector of FIGS. 2 and 3.

With particular reference to FIGS. 3-5, further details of clevis 150 are described. As shown, each of first opening 152 and second opening 154 are offset a distance "cd" from a plane "B," which is defined between a tissue-contacting surface 131 of first jaw member 130 and a tissue-contacting surface 141 of second jaw member 140 when jaw members 130, 140 are in the approximated position (FIG. 3). That is, the first and second pivot axes defined by pivot pins 127 and 128, respectively, are offset from the longitudinal axis "A-A."

More particularly, first opening 152 of clevis 150 is disposed on a first side of plane "B," and second opening 154 of clevis 150 is disposed on a second, opposite side of plane "B." A center of each opening 152, 154 may be offset a distance "cd" of about 0.005 inches from the plane "B." Larger or smaller offset distances are contemplated.

The orientation and offsetting of first opening 152 and second opening 154 with respect to plane "B" help optimize (e.g., maximize) the pressure applied between jaw members 130, 140. Moreover, the offsetting of openings 152, 154 increases the angle θ of links 160 and 170, respectively, when jaw members 130, 140 are in the approximated position (FIG. 3), thus resulting in an optimization of pressure. Angle θ may be between about 10° and about 30°. In one embodiment, angle θ is about 15°. Larger and smaller angles are also contemplated. In some embodiments, a larger angle θ results in an application of greater pressure across pivot pin (e.g., 127) as the component vector of pressure in the longitudinal direction about the moment is increased.

Figure 7:
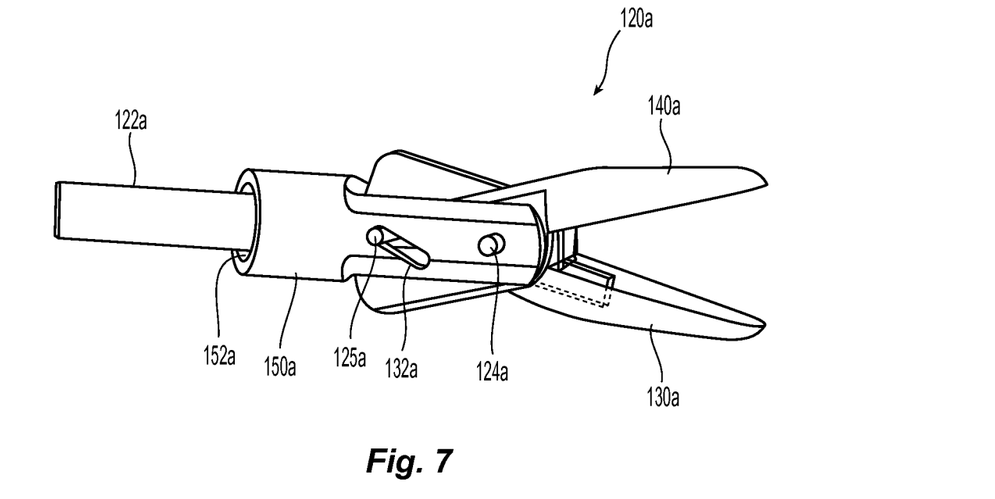
FIG. 7 is a side, cut-away view of an end effector of the surgical instrument of FIG. 1 in accordance with an alternate embodiment of the present disclosure.

FIG. 7 illustrates an alternate embodiment of an end effector 120a for use with surgical instrument 100. End effector 120a includes a first jaw member 130a, a second jaw member 140a, and a clevis 150a. A pivot pin 124a extends through a distal opening (not explicitly shown) of each jaw member 130a, 140a, such that jaw members 130a, 140a are pivotal with respect to each other about pivot pin 124a.

Each jaw member 130a, 140a also includes a cam slot 132a (the cam slot of jaw member 140a is hidden from view in FIG. 7) extending through a proximal portion thereof. Control rod 122a of this embodiment includes a pair of cam followers 125a extending laterally therefrom (one cam follower is hidden from view in FIG. 7). One cam follower 124a engages cam slot 132a of first jaw member 130a, and the other cam follower engages the cam slot of the second jaw member 140a. Alternatively, a single cam follower 124a extends from control rod 122a and engages both jaw members 130a, 140a. Additionally, control rod 122a is longitudinally translatable through a proximal opening 152a in clevis 150a.

In use, longitudinal translation of control rod 122a causes cam follower(s) 124a to travel through respective cam slots 132a to pivot the jaw members 130a, 140a between open and approximated positions. More particularly, distal translation of control 122a with respect to clevis 150a causes cam follower 124a to travel distally through cam slot 132a, thus approximating the jaw members 130a, 140a. Proximal translation of control rod 122a with respect to clevis 150a causes cam follower 124a to travel proximally through cam slot 132a, thus opening the jaw members 130a, 140a.

Referring back to FIG. 6, further details of jaw member 130 and its electrical isolation features are discussed herein. Jaw member 130 of FIG. 6 includes a support surface 133 and an active electrode seal plate 135 coupled to support surface 133, and electrically isolated from support surface 133. Active electrode seal plate 135, which may act as a first electrical potential, is disposed in electrical communication (e.g., via a wire) with a source of electrosurgical energy.

For one embodiment, to achieve the electric isolation, various manufacturing steps are taken. Support surface 133 is coated with a high temperature dielectric material (e.g., parylene, polyimide, fluoropolymer, ceramic, etc.). Additionally, active electrode seal plate 135 is bonded to support surface 133 using a high temperature, dielectric epoxy. A particularly suitable epoxy has a comparative tracking index of greater than 600V and/or is capable of withstanding 200 degrees Celsius. Alternatively or additionally, a polyimide backing film may be positioned between active elective seal plate 135 and support surface 133 to provide further electric isolation. Here, when using polyimide backing film, an epoxy bond layer may be used over a top surface of the polyimide to ameliorate surface tracking.

Further, while the discussion regarding FIG. 6 describes jaw member 130, second jaw member 140 may include the same or similar features. Here, the second electrical potential would include the electrode seal plate disposed on the second jaw member 140.

Second jaw member 140 may be configured differently and include a separate support surface 133 and active electrode seal plate 135 (see FIG. 8). Rather, the second electrical potential may be conducted through control rod 122, clevis 150, and second link 170 to second jaw member 140. Here, tissue-contacting surface 141 of second jaw member 140 may conduct current directly to tissue held between jaw members 130, 140.

Additionally, first jaw member 130 and/or second jaw member 140 may utilize a printed conductive ink as the electrode when that particular jaw member 130, 140 includes a support surface and an active electrode seal plate, as described above.

In an alternate embodiment, first jaw member 130 and/or second jaw member 140 are made from a dielectric material (e.g., PEEK (PolyEtherEther-Ketone), Torlon® (polyamide-imide; a high-strength plastic), ceramic, etc.) and a laminated electrode seal plate is adhered to the tissue-contacting surface 131, 141 of the respective jaw member 130, 140.

Referring now to FIGS. 6 and 8, first jaw member 130 (FIG. 6) and second jaw member 140 (FIG. 8) are shown. Each jaw member 130, 140 includes a respective flange 137, 147 extending from support surface 133, 143, respectively, which is perpendicular or substantially perpendicular to respective tissue-contacting surfaces 131, 141. Flanges 137, 147 include a thickness "ft" of between about 0.010 inches and about 0.015 inches. In one embodiment, thickness "ft" of flanges 137, 147 is about 0.012 inches.

With continued reference to FIGS. 6 and 8, each jaw member 130, 140 includes a knife slot 139, 149, respectively. As shown, a proximal end of each knife slot 139, 149 extends proximally of respective distal pivot openings 134, 144, about which the jaw members 130, 140 pivot with respect to each other. The location of knife slots 139, 149 helps support flanges 137, 147, respectively and help improve yield strength of jaw members 130, 140. The location of knife slots 139, 149 also helps guide a knife 180 (FIGS. 9 and 10) from its fully retracted position to its fully extended position.

Figure 9:
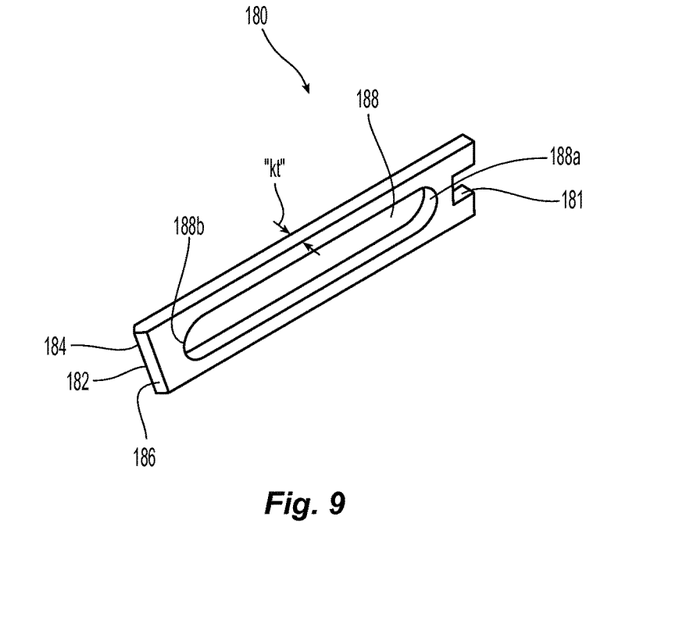
FIG. 9 is a perspective view of a knife of the surgical instrument of FIG. 1 in accordance with embodiments of the present disclosure.
Figure 10:
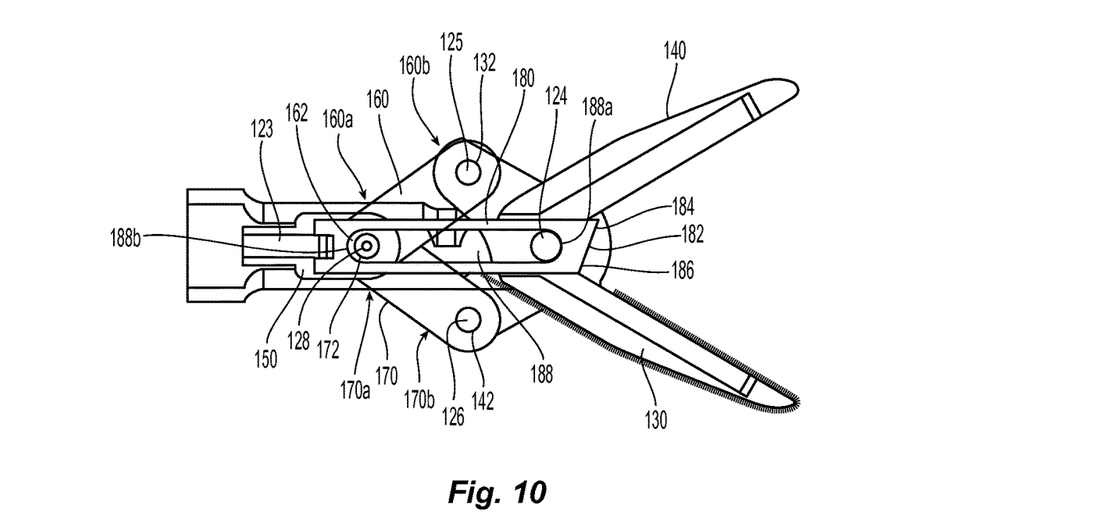
FIG. 10 is a side, cut-away view of the end effector of the surgical instrument of FIG. 1 including the knife of FIG. 9.

With reference to FIGS. 9 and 10, knife 180 is shown. Knife 180 is longitudinally translatable with respect to jaw members 130, 140. Distal translation of knife 180 cuts tissue disposed between jaw members 130, 140. A distal cutting edge 182 of knife 180 includes a tapered surface such that a first, upper portion 184 of cutting edge 182 extends farther distally than a second, lower portion 186 of cutting edge 182. The tapered surface of cutting edge 182 pushes tissue toward first jaw member 130 as knife 180 is translated distally.

Knife 180 also includes a slot 188 therein. As shown in FIG. 10, pivot pin 124 extends through slot 188. The engagement between pivot pin 124 and slot 188 constrains the longitudinal travel of knife 180. More particularly, when knife 180 is retracted towards its proximal-most position (FIG. 10), pivot pin 124 contacts a distal end 188a of slot 188, thus preventing further retraction of knife 180. When knife 180 is extended toward its distal-most position, pivot 124 contacts a proximal end 188b of slot 188, thus preventing further advancement of knife 180.

A proximal end of knife 180 includes a notch 181 configured to engage a knife rod 123 (FIGS. 9 and 10) of surgical instrument 100. Translation of knife rod 123 results in a corresponding translation of knife 180.

Knife 180 may be made from stainless steel (e.g., 400 series) or other suitable materials. Additionally a knife thickness "kt" may be about 0.009 inches, and a slot thickness "st" (FIG. 8), through which knife 800 travels may be about 0.015 inches. Accordingly, the aspect ratio of slot thickness "st" to knife thickness "kt" may be less than 2:1.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
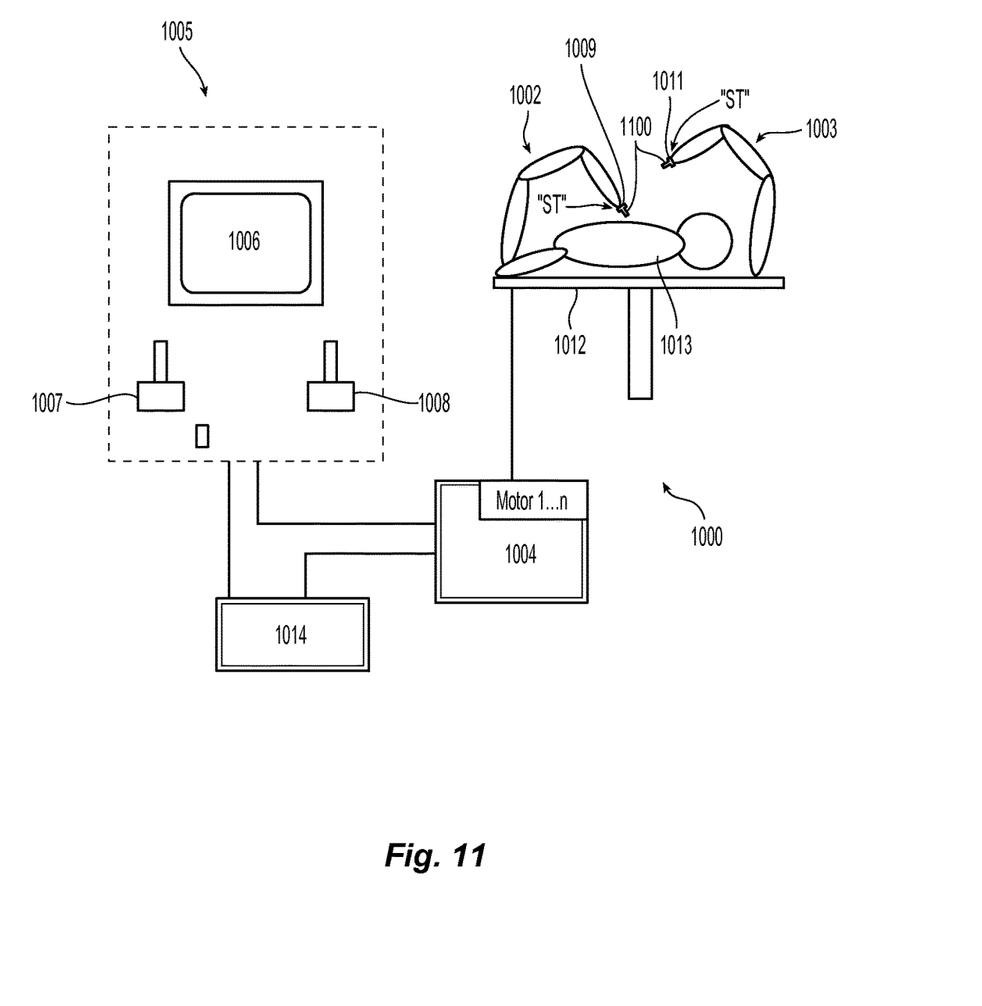
FIG. 11 is a schematic illustration of a surgical system in accordance with the present disclosure.

With particular reference to FIG. 11, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical tool "ST" (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic surgical instrument, comprising:
a housing;
a handle movably connected to the housing;

an elongated shaft extending distally from the housing and defining a longitudinal axis;

an end effector assembly disposed adjacent a distal end of the elongated shaft, the end effector assembly including a first jaw member and a second jaw member, at least one of the jaw members movable with respect to the other jaw member from a spaced-apart position wherein the jaw members are spaced relative to one another to a grasping position wherein the jaw members are parallel to one another for grasping tissue;

a drive assembly disposed at least partially within the housing, the drive assembly including a drive bar extending at least partially through the elongated shaft such that longitudinal translation of the drive bar causes the jaw members to move between the spaced-apart position and the grasping position;

a clevis disposed adjacent a distal portion of the drive bar;

a first link pivotably connected to the clevis about a first pivot axis, and pivotably connected to the first jaw member about a first jaw member pivot, the first link disposed at a non-parallel angle relative to the longitudinal axis when the jaw members are in the grasping position; and a second link pivotably connected to the clevis about a second pivot axis, and pivotably connected to the second jaw member about a second jaw member pivot, wherein the first pivot axis and the second pivot axis are offset from the longitudinal axis.

2. The endoscopic surgical instrument according to claim 1, wherein the first pivot axis is offset from the longitudinal axis by a distance of about 0.005 inches.

3. The endoscopic surgical instrument according to claim 2, wherein the second pivot axis is offset from the longitudinal axis by a distance of about 0.005 inches.

4. The endoscopic surgical instrument according to claim 1, wherein the first pivot axis is on a first side of the longitudinal axis, and wherein the second pivot axis is on a second side of the longitudinal axis.

5. The endoscopic surgical instrument according to claim 1, wherein a diameter of the elongated shaft is about 2.4 mm.

6. The endoscopic surgical instrument according to claim 1, wherein a majority of the elongated shaft has a constant diameter of about 2.4 mm.

7. The endoscopic surgical instrument according to claim 1, wherein the drive assembly is configured to apply pressure between the jaw members in the range of about 3 kg/cm² to about 16 kg/cm².

8. The endoscopic surgical instrument according to claim 1, wherein the first jaw member includes a support surface and an active electrode seal plate.

9. The endoscopic surgical instrument according to claim 8, wherein the active electrode seal plate is bonded to the support surface with a high-temperature, dielectric epoxy.

10. The endoscopic surgical instrument according to claim 8, wherein the support surface is coated with a high-temperature dielectric material.

11. The endoscopic surgical instrument according to claim 1, wherein at least a portion of the first jaw member is coated with a high-temperature dielectric material.

12. The endoscopic surgical instrument according to claim 11, wherein an entirety of the second jaw member lacks a high-temperature dielectric material.

13. The endoscopic surgical instrument according to claim 1, wherein the first jaw member is connected to the second jaw member with a pivot pin.

14. The endoscopic surgical instrument according to claim 13, wherein the pivot pin is disposed distally of the first jaw member pivot.

15. The endoscopic surgical instrument according to claim 13, further comprising a knife configured to sever tissue, wherein the first jaw member includes a knife slot defined therein and configured to guide longitudinal translation of the knife, and wherein a proximal end of the knife slot is disposed proximally of the pivot pin.

16. The endoscopic surgical instrument according to claim 13, wherein the first jaw member includes a tissue-contacting surface and a flange extending perpendicularly from the tissue-contacting surface, wherein the pivot pin extends through an opening in the flange.

17. The endoscopic surgical instrument according to claim 16, wherein the flange includes a thickness of about 0.012 inches.

18. The endoscopic surgical instrument according to claim 1, wherein the first jaw member pivot is movable toward and away from the longitudinal axis.

19. The endoscopic surgical instrument according to claim 1, wherein the second link is disposed at a non-parallel angle relative to the longitudinal axis when the jaw members are in the grasping position.

20. The endoscopic surgical instrument according to claim 19, wherein the first link is disposed at a non-parallel angle relative to the second link when the jaw members are in the grasping position.

21. An endoscopic surgical instrument, comprising:

a housing;

a handle movably connected to the housing;

an elongated shaft extending distally from the housing and defining a longitudinal axis, the elongated shaft including a diameter of about 2.4 mm along at least a majority of an entire length thereof;

an end effector assembly disposed adjacent a distal end of the elongated shaft, the end effector assembly including a first jaw member and a second jaw member, at least one of the jaw members movable with respect to the other jaw member from a spaced-apart position wherein the jaw members are spaced relative to one another to a grasping position wherein the jaw members are closer to one another for grasping tissue; and a drive assembly disposed at least partially within the housing, the drive assembly including a drive bar extending at least partially through the elongated shaft such that longitudinal translation of the drive bar causes the jaw members to move between the spaced-apart position and the closer position for grasping tissue, wherein the drive assembly is configured to apply pressure between the jaw members in the range of about 3 kg/cm² to about 16 kg/cm².

22. The endoscopic surgical instrument according to claim 21, wherein at least a portion of the first jaw member is coated with a high-temperature dielectric material, and wherein an entirety of the second jaw member lacks a high-temperature dielectric material.

* * * * *

EX PARTE REEXAMINATION CERTIFICATE (11704th)
United States Patent
Schechter et al.

(10) Number: US 10,154,877 C1
(45) Certificate Issued: Jul. 27, 2020

(54) ENDOSCOPIC SURGICAL INSTRUMENT

(71) Applicant: COVIDIEN LP, Mansfield, MA (US)

(72) Inventors: David A. Schechter, Boulder, CO (US); Nathan White, Longmont, CO (US); Joshua K. Goetz, Broomfield, CO (US)

(73) Assignee: COVIDIEN LP, Mansfield, MA (US)

Reexamination Request:
No. 90/014,422, Dec. 20, 2019

Reexamination Certificate for:
Patent No.: 10,154,877
Issued: Dec. 18, 2018
Appl. No.: 14/932,302
Filed: Nov. 4, 2015

(51) Int. Cl.
*A61B 18/14* (2006.01)
*A61B 34/37* (2016.01)
*A61B 17/29* (2006.01)
*A61B 18/00* (2006.01)

(52) U.S. Cl.
CPC .......... *A61B 18/1445* (2013.01); *A61B 34/37* (2016.02); *A61B 2017/294* (2013.01); *A61B 2017/2936* (2013.01); *A61B 2017/2947* (2013.01); *A61B 2018/00428* (2013.01); *A61B 2018/1455* (2013.01)

(58) Field of Classification Search
None
See application file for complete search history.

(56) References Cited

To view the complete listing of prior art documents cited during the proceeding for Reexamination Control Number 90/014,422, please refer to the USPTO's public Patent Application Information Retrieval (PAIR) system under the Display References tab.

*Primary Examiner* — Beverly M Flanagan (57) ABSTRACT

An endoscopic surgical instrument is provided. The instrument includes a housing, a handle, an elongated shaft extending distally from the housing and defining a longitudinal axis, an end effector assembly, a drive assembly, a clevis, a first link, and a second link. The end effector assembly is disposed adjacent a distal end of the elongated shaft and includes a first jaw member and a second jaw member. The first link is pivotably connected to the clevis about a first pivot axis, and is pivotably connected to the first jaw member about a first jaw member pivot. The second link is pivotably connected to the clevis about a second pivot axis, and is pivotably connected to the second jaw member about a second jaw member pivot. The first pivot axis and the second pivot axis are offset from the longitudinal axis.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-22 is confirmed.

\* \* \* \* \*